United States Patent [19]

Bartos et al.

[11] Patent Number: 5,324,636
[45] Date of Patent: Jun. 28, 1994

[54] RADIORESPIROMETER AND METHOD OF USE

[75] Inventors: Dagmar Bartos, Portland; Donald D. Trunkey, Oregon City; Angelo A. Vlessis, Portland, all of Oreg.

[73] Assignee: The State of Oregon Acting by and Through the State Board of Higher Education on Behalf of Oregon Health Sciences University, Portland, Oreg.

[21] Appl. No.: 31,032
[22] Filed: Mar. 11, 1993

Related U.S. Application Data

[63] Continuation of Ser. No. 735,390, Jul. 24, 1991, abandoned.

[51] Int. Cl.$^5$ .......................... C12M 1/34; C12Q 1/16
[52] U.S. Cl. ........................................ 435/35; 435/39; 435/291; 435/298; 435/807; 435/284; 422/88; 422/102
[58] Field of Search .......... 435/29, 31, 32, 34, 435/35, 39, 40, 284, 285, 291, 296–298, 299–301, 807, 808, 810; 422/88, 102; 436/32, 57, 63, 133, 167, 168; 250/390.11; 356/244, 246

[56] References Cited

U.S. PATENT DOCUMENTS

| | | | |
|---|---|---|---|
| 2,144,255 | 1/1939 | Carpenter | 435/298 |
| 2,533,088 | 12/1950 | Brewer et al. | 435/298 |
| 2,694,033 | 11/1954 | Fletcher | 435/298 |
| 2,971,892 | 2/1961 | Carski | 435/298 |
| 3,055,808 | 9/1962 | Henderson | 435/298 |
| 3,337,416 | 8/1967 | Forgacs | 435/294 |
| 3,769,936 | 11/1973 | Swanson et al. | 119/15 |
| 3,819,489 | 6/1974 | Kronick et al. | 435/35 |
| 3,935,449 | 1/1976 | Reunanen | 250/252.1 |
| 3,941,660 | 3/1976 | Mirsky | 435/35 |
| 3,944,471 | 3/1976 | Waters | 435/35 |
| 3,968,010 | 7/1976 | Young | 435/34 |
| 3,990,852 | 11/1976 | Piazzi et al. | 422/102 |
| 3,997,404 | 12/1976 | Waters | 435/35 |
| 4,057,470 | 11/1977 | Schrot | 435/298 |
| 4,237,234 | 12/1980 | Meunier | 435/301 |
| 4,246,352 | 1/1981 | Buddemeyer | 435/35 |
| 4,419,451 | 12/1983 | Garner et al. | 435/298 |
| 4,590,158 | 5/1986 | Eikman | 435/35 |
| 4,668,633 | 5/1987 | Walton | 435/298 |
| 5,034,331 | 7/1991 | Brewer | 435/298 |

OTHER PUBLICATIONS

Spahr et al., "Substrate Oxidation by Adult Cardiomyocytes in Long-term Primary Culture," J. Mol. of Mol. Cell Cardiol. 21:175–185 (1989).
Pardridge et al., "Branched Chain Amino Acid Oxidation in Cultured Rat Skeletal Muscle Cells," J. Clin. Invest. 66:88–93 (Jul. 1980).
Shaw et al., "Effect of Insulin on Pyruvate and Glucose Metabolism of Beating Mouse Heart Cells," J. of Mol. Cell Cardiol. 4:485–495 (1972).
Ross et al., "Radiorespirometry and Metabolism of Cultured Cells Attached to Petri Dishes," Anal. Biochem. 112:378–386 (1981).
Wang, "Radiorespirometry," Methods of Biochemical Analysis 15:311–368 (1967).

Primary Examiner—Michael G. Wityshyn
Assistant Examiner—William H. Beisner
Attorney, Agent, or Firm—Klarquist Sparkman Campbell Leigh & Whinston

[57] ABSTRACT

A simple device functioning as a radiorespirometer is a petri dish with a modified cover for quantitating an amount of $CO_2$ evolved by living cultured cells. The device is a plastic culture dish having a culture surface circumscribed by a continuous sidewall. A removable flat plastic cover has a flat inside face and an annular collar around the face that fits against a sidewall. The collar is maintained in substantially gas-tight relationship against the sidewall by an elastic band or tightly mating surfaces. An opening through the cover is sealed by a gas-impervious material, such as a plastic film, that can be penetrated by a needle to introduce acid into the dish for terminating culture growth and lysing the cells. A collector tube is removably secured to the inside face of the cover and contains a $CO_2$ trapping material, such as hyamine (methylbenzethonium hydroxide). The culture medium is provided with a cell substrate that contains radioactive carbon, and radioactive $CO_2$ produced by the cells is then collected by the hyamine in the tube. The cover is afterwards removed from the dish, and the tube is detached from the cover and placed in a liquid scintillator to quantitate the amount of radioactive $CO_2$ contained in the liquid.

21 Claims, 3 Drawing Sheets

U.S. Patent    June 28, 1994    Sheet 1 of 3    5,324,636
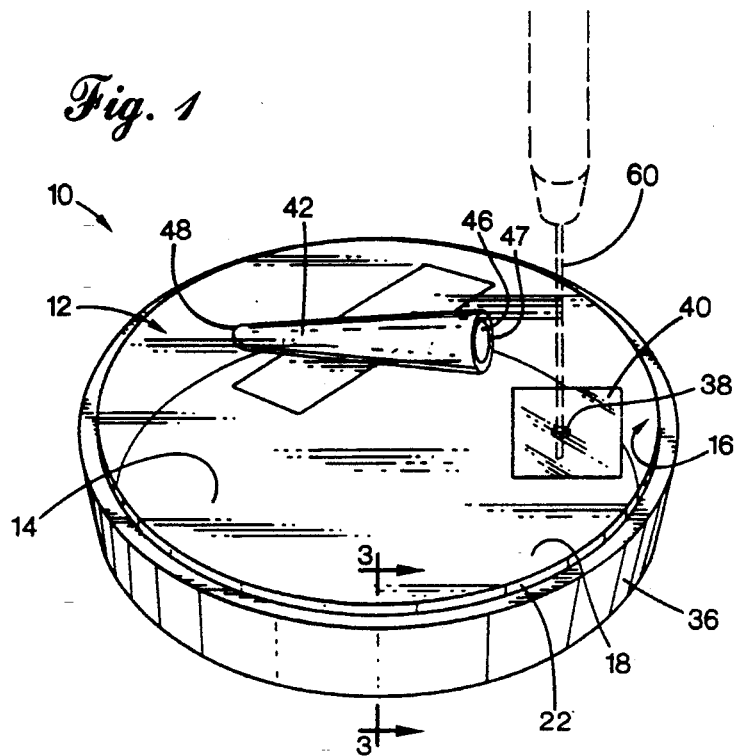
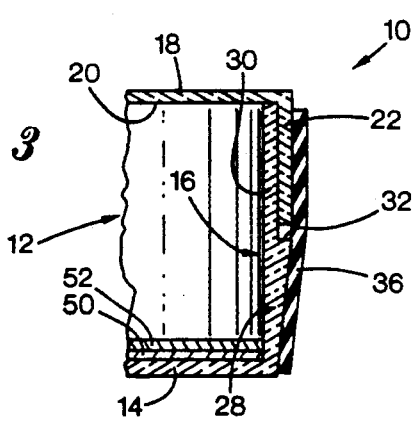
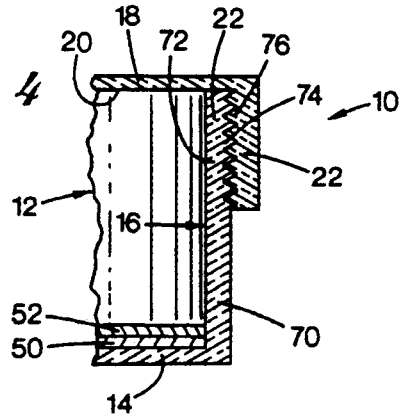
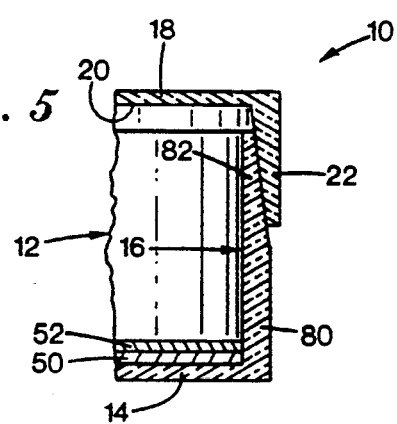

RADIORESPIROMETER AND METHOD OF USE

This application is a continuation of application Ser. No. 07/735,390, filed on Jul. 24, 1991, now abandoned.

BACKGROUND OF THE INVENTION

1. Field of the Invention

This invention concerns a device for measuring an amount of gas evolved by cultured cells, and more particularly concerns a radiorespirometer that measures $^{14}CO_2$ production for studying the metabolism of cultured cells.

2. General Discussion of the Background

Oxidation rates of various metabolic pathways of intact cells are determined by measuring $^{14}CO_2$ released from cultured cells. The activity of pyruvate dehydrogenase, for example, can be determined by culturing cells in the presence of radiolabeled [—$^{14}C$]-pyruvate, denaturing cells by acidification with $HClO_4$, and collecting liberated $^{14}CO_2$ from decarboxylated pyruvate in a vial containing a material that sequesters the $^{14}CO_2$. The amount of liberated $^{14}CO_2$ is then quantitated by placing the vial in a liquid scintillation counter to determine the amount of radioactivity that is present, which in turn indicates the amount of $^{14}CO_2$ that was evolved.

Previous radiorespirometers, and other measurement methods, have involved complex and awkward devices that limit the amount of data that can be collected. Some prior methods require that cells be removed from a petri dish by scraping them from the culture surface, which mechanically injures the cells and disturbs their normal physiology. In other methods, a non-cellular extract is obtained from the cells, and the extract is used to measure enzymatic production of $^{14}CO_2$ from $^{14}C$ substrate. Producing non-cellular extracts requires cell disruption that interferes with normal cell metabolism. The resulting data may be biased by the metabolic contribution of damaged cell material.

An example of a previous radiorespirometer was described by Ross et al. in *Analytical Biochemistry* 112:378–386 (1981). This radiorespirometer is an airtight chamber created by placing a culture plate in a well and clamping a stainless steel cover over the well. A carrier gas is bubbled through the growth medium in the dish to entrain $^{14}CO_2$ and remove it from the culture chamber. The radioactive gas is then taken to an external collection chamber where a $CO_2$ trapping agent (Oxisorb II) collects the gas in a scintillation vial. The vial is subsequently placed in a liquid scintillator to measure the amount of radioactivity present in the sample. The usefulness of this design is limited by its complexity and the requirement for many airtight chambers.

Another approach to quantitative measurement of substrate oxidation was disclosed in Spahr et al., *J. Mol. Cell Cardiol.* 21:175–185 (1989), where degradation and oxidation of substrates were estimated using U-$^{14}C$-labeled glucose, lactate and palmitate. Each petri dish containing attached cells was placed in individual airtight chambers and the substrate oxidation was terminated by injecting HCl through a rubber stopper in the cover of an airtight chamber. Radioactive carbon dioxide was then trapped in a KOH solution contained in a reservoir within each incubation chamber.

Shaw and Boder described another method in *J. Mol. Cell. Cardiol.* 4:485–493 (1972) in which evolution of $^{14}CO_2$ from growing myocytes was measured in a stoppered flask by suspending a plastic collector cup from the rubber stopper of the flask. Although measurements on intact cultured cells can be obtained with such a device, culturing cells in flasks requires a larger number of cells than are required in smaller containers. The number of flasks containing the cells prepared from the same isolation is therefore small, which limits the number of experimental points generated for the cell sample. In addition, many non-malignant cells will not grow or survive in a culture flask.

It is accordingly an object of the present invention to provide an improved simple device in which evolution of gas from living cells can be detected without requiring a complicated apparatus.

It is yet another object of the invention to provide such an improved device that allows many cell cultures from a given isolation to be simultaneously studied, thereby generating larger volumes of data.

Yet another object of the invention is to provide such an improved device in which studies can be performed on physiologically and biochemically intact attached cells.

Finally, it is an object of the invention to provide such an improved device in which the accuracy of data is improved by reducing the metabolic contribution of damaged cell materials.

These and other objects of the invention will be understood more clearly by reference to the following detailed description and drawings.

SUMMARY OF THE INVENTION

The foregoing objects are achieved by providing a substantially gas-tight culture chamber that includes a culture surface surrounded by one or more walls enclosing the chamber. A gas-trapping container is attached to an inside wall of the chamber. A substantially gas-impermeable liquid port communicates with the chamber and provides access for introducing a reaction stopping liquid, such as an acid solution, into the chamber for terminating the experiment.

In preferred embodiments, the device is a plastic culture dish that includes a culture surface circumscribed by a continuous sidewall. A removable flat culture dish cover has a peripheral collar that mates with the sidewall, and an inside face that is spaced above the culture surface. The device is maintained substantially gas-tight by placing an elastic band around the collar and sidewall. Alternatively, a gas-tight relationship is maintained by providing mating screw threads on the collar and sidewall, or by reciprocally tapering opposing surfaces on the cover and sidewall. The liquid port is an opening through the cover that is sealed by a gas-impervious material, such as plastic adhesive tape, that can be penetrated by a needle. A collector tube is removably secured parallel to the inside face of the cover by another piece of adhesive plastic tape.

The present invention includes a radiorespirometry method for quantitating an amount of carbon dioxide evolved by living cells. The method includes the steps of culturing the cells in a culture dish with a substrate that contains a radioactive carbon atom. The dish includes a culture surface circumscribed by a continuous sidewall that mates with a cover having an inside face against which a collector tube is selectively secured. The tube contains a substance, such as an organic base, that traps $CO_2$. The cells are then incubated, and evolved $^{14}CO_2$ is trapped in the collector tube secured to the inside face of the cover.

Substrate utilization by culture cells is terminated by inserting a needle through the plastic film that seals the opening and injecting a sufficient amount of a denaturing solution, such as an acid, to terminate the reaction(s). The plastic film is then resealed, and $CO_2$ collection continued for a preselected period. The cover is then removed from the dish and the collector tube is detached from the inside cover face and placed in a liquid scintillator to quantitate the amount of radioactive $CO_2$ contained in the liquid.

BRIEF DESCRIPTION OF THE DRAWINGS

FIG. 1 is a top perspective view of a radiorespirometer of the present invention, in which a hypodermic needle is shown placed in phantom through an injection port in the cover of a dish.

FIG. 3 is a fragmentary, cross-sectional view taken along section lines 3—3 in FIG. 1, showing placement of an elastic band around the periphery of the dish.

FIG. 4 is a view similar to FIG. 3, showing an alternative screw top embodiment of the dish.

FIG. 5 is another view similar to FIG. 3, showing yet another alternative embodiment of the invention in which cooperatively tapering faces of the cover and sidewall seal the dish.

DETAILED DESCRIPTION OF PREFERRED EMBODIMENTS

Figure 2:
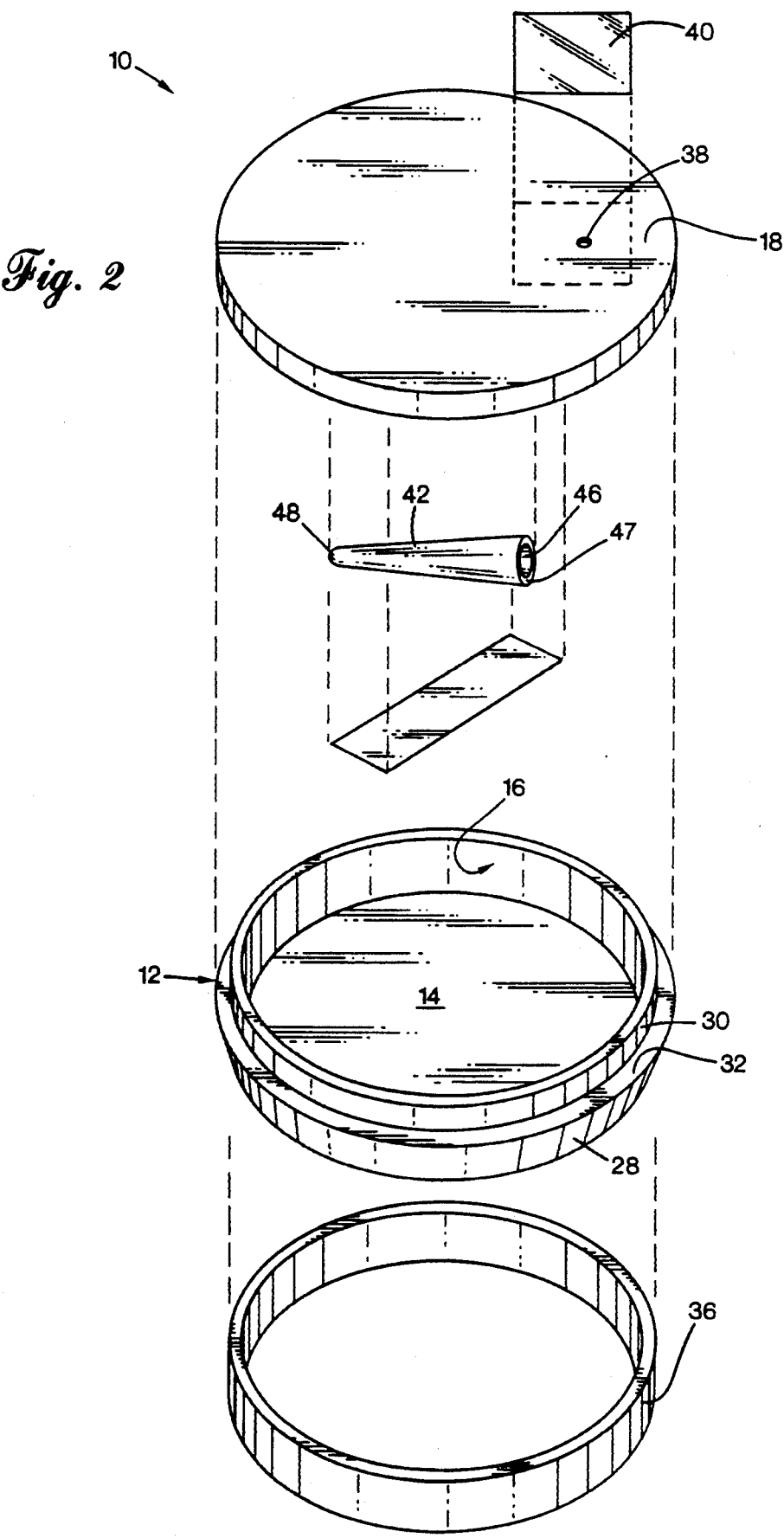
FIG. 2 is an exploded view of the radiorespirometer shown in FIG. 1, the hypodermic needle not being shown.

A radiorespirometer 10 is shown in FIGS. 1 and 2 to include a plastic culture dish 12 in which a disk-shaped culture surface 14 is circumscribed by an arcuate continuous sidewall 16. A removable flat, circular, clear plastic dish cover 18 has an inside face 20 (FIG. 3) and a circumferential depending collar 22 that abuts circumferentially against sidewall 16. The sidewall 16 includes a base portion 28 and a mating portion 30. Sidewall 16 increases in thickness as it moves away from surface 14, but then abruptly decreases in thickness at the origin of mating portion 30 such that a right angle step 32 is formed. The inside face of collar 22 abuts circumferentially against the outside face of mating portion 30 above step 32 to hold cover 18 in place on dish 12.

A continuous circular flexible elastic band 36 fits tightly around the outside circumference of dish 12. Band 36 has a diameter small enough to fit tightly against base portion 28 and collar 22 to form a substantially gas-tight seal. The elasticity of band 36 is great enough that the band can stretch sufficiently to be removed from around dish 12. In the absence of the elastic band, cover 18 can be freely removed from dish 12 to gain access to the interior of the respirometer. However, once the band is stretched into position around sidewall 16 and collar 22, as shown in FIGS. 1 and 3, the cover 12 is tightly secured to the dish such that gas evolved by cells on surface 14 cannot escape to the atmosphere. The elastomeric seal provided by band 36 need not be perfectly hermetic, but substantial retention of evolved gas in the chamber of the dish is sufficient.

A small, circular port 38 is provided through cover 18 such that an acid solution can be introduced into dish 12 to terminate cell growth. The port is sealed by a rectangular, substantially gas-impervious plastic film 40, for example a segment of transparent adhesive plastic tape, placed on top of the outer surface of cover 18. A collector tube 42 is secured against the inside face 20 of the cover 18 by a rectangular strip of transparent plastic adhesive tape 44. Tube 42 is a 250 μl volume plastic mini test tube having a tapering outer body that surrounds a central bore 46 that tapers from an open mouth 47 to a closed end 48. Tube 42 is secured against the inside face 20 of cover 18 such that bore 46 is substantially parallel to the plane of face 20.

Tube 42 contains a carbon dioxide trapping material, preferably a high viscosity organic base such as methylbenzethonium hydroxide (available from Sigma Chemical Company as hyamine hydroxide). Other suitable bases include KOH, NaOH, phenylethylamine, and diphenylethylamine. Capillary tension of the liquids keeps solutions securely in the plastic mini test tube. Tube 42 is, for example, a polyethylene Eppendorf tube that can be obtained from Brinkmann Instruments, Inc., under catalogue no. 022-36-440-5. Such a tube has a plastic cap that is removed and not used with the tube 42.

In the method of the present invention, the amount of carbon dioxide evolved by living cells is quantitated by culturing cells in a culture dish 12 in the presence of a substrate containing a radioactive carbon atom. The cells can be cultured in a conventional petri dish attached to the inside face of bottom surface 14, to form a confluent cell layer 50. Any suitable culture medium (FIGS. 3-5) can be provided in an overlying layer of medium 52, such as Dulbecos Modified Eagles/F12 medium (Gibco) for culturing myocytes. Cells are cultured in medium 52 to form confluent cell layer 50 after several days to weeks of growth. The culture can then be washed with a buffer and suctioned to remove the culture media and any protein in the medium that could confound later measurements.

A radioactively labeled substrate is then added to the culture by providing a new incubation buffer or fresh culture medium that contains the labeled substrate. The identity of the labeled substrate varies depending on the biological system or reaction being studied. Radioactive pyruvate ($[1—^{14}]$-pyruvate), for example, is added to study the activity of pyruvate dehydrogenase. A radiolabeled ornithine substrate could be used to study ornithine decarboxylase activity, or radioactively labeled amino acids ($C^{14}$ glucose, $^{14}C$ fatty acids) to measure utilization/oxidation of these energy and $^{14}CO_2$ producing compounds.

Immediately after addition of the radiolabeled substrate, the petri dish cover 18, with the attached mini test tube 42 containing an organic base (prepared before the experiment), is placed in substantially gas-tight relationship against sidewall 16 with tube 42 adhered against face 20 with adhesive tape 40. Cover 18 is held in substantially gas-tight relationship against sidewall 16 by securing elastic band 36 around the circumference of dish 12 such that band 36 fits tightly against collar 22 and base portion 28 (FIG. 3). After cover 18 is secured against sidewall 16 and sealed with band 36, the culture will continue to grow as long as oxygen is present, for example about one hour for myocytes. The experiment is then terminated by inserting a needle 60 through film 40 and port 38, and injecting a sufficient amount of a denaturing solution into the incubation. Suitable reaction terminating solutions include acids, such as 50% $HClO_4$, 1M HCl, 1M citric acid, sulfuric acid, trichloroacetic acid, or 2M sodium acetate, which displace $CO_2$ from bicarbonate in the buffered medium.

After needle 60 is withdrawn, the resulting needle hole in film 40 is closed immediately by placing a segment of adhesive plastic tape over the hole to prevent escape of $CO_2$ from the incubation chamber. After acidification and denaturation of cells, $CO_2$ collection is allowed to continue for one hour to release all generated $CO_2$. Cover 18 is then removed from dish 12 by pulling band 36 away from collar 22 and base portion 28, and lifting cover 18. Tube 42 is then detached from inside face 20 by peeling tape 44 away from the face. Tube 42 is placed in a liquid scintillator and the amount of evolved radioactive $CO_2$ is quantitated in a conventional manner.

The foregoing method may be better understood by reference to the following example.

EXAMPLE I

Pyruvate dehydrogenase (PDH) activity was determined in cultured myocytes as well as in freshly isolated cardiac mitochondria using [1—$^{14}$C]-pyruvate. Adult cardiac myocytes were isolated and cultured using a modification of the technique described by Nag and Cheng in *Tissue and Cell* 13:515-523 (1981). Adult male Sprague-Dawley rats (300-350 g) Were heparinized with 1500 units intraperitoneally. Thirty minutes later, animals were sacrificed by decapitation and the ascending aorta was rapidly canalized ($<15$ seconds). The heart was immediately perfused with 10 ml of ice cold, $Ca^{2+}$-free Krebs-Henseleit (KH) buffer, rapidly attached to a pulsatile perfusion apparatus and perfused (3 ml/minute) under aseptic conditions with oxygenated KH buffer plus 50 $\mu$M $CaCl_2$ and collagenase (150 U/ml) at 37° C. After 45 minutes, the gelatinous ventricular myocardium was excised and minced in a petri dish containing the digestive buffer. Cells were rinsed through a fine wire mesh screen into a 30 ml Corex tube. After two additional rinses, viable cells were obtained by centrifugation at 300 g on a 1:1 isotonic Percoll:KH Buffer gradient.

The pellet was collected and rinsed twice with KH buffer plus 1.4 mM $CaCl_2$ and 2% fatty acid free bovine serum albumin. Percent viability ranged between 60-80% as determined by trypan blue exclusion. Cells were plated onto collagen coated petri dishes, 100,000 viable cells/3 cm dish. Cultures were maintained at 37° C. in an atmosphere of 5% $CO_2$, 95% air in Dulbecos Modified Eagles/F12 Medium (Gibco) plus 1.4 mM $CaCl_2$, 10% fetal bovine serum, 60 $\mu$g/ml endothelial cell growth supplement (Collaborative Research Inc.), 1 $\mu$l/ml ITS Premix (Collaborative Research Inc.) and 7 mg/l cytosine arabinoside (to prevent fibroblast proliferation). Seven days post-isolation, cytosine arabinoside was withheld from the culture medium and 12-14 days post-isolation the cultures were employed for experimentation.

Cultured myocytes were placed in KH buffer with 5 mM pyruvate and 1.4 mM $CaCl_2$ after gentle washing. Radio labelled [1—$^{14}$C]-pyruvate (0.1 microcuries, 10 $\mu$M) and tBOOH (0-200 $\mu$M) were added simultaneously to the culture dish. Tube 42 (containing the organic base hyamine) was taped to the inside face of cover 18, and the cover set in place on dish 12. Dishes were then sealed with rubber elastic band 36 and incubated at 37° C. for 30 minutes. Cells were denatured by acidification by adding 50 microliters of 50% $HClO_4$ via a sealed injection port. The $^{14}CO_2$ liberated from decarboxylated pyruvate was collected in a small hyamine-containing vial attached to the inside cover of the petri dish. The vial was detached from the cover and radioactivity was counted using the Beckman LS 9000 scintillation counter. The peroxide-induced non-enzymatic decarboxylation of pyruvate was controlled as previously described by Vlessis et al. in *Biochem. Biophys. Res. Commun.* 170:1281-1287 (1990).

Figure 6:
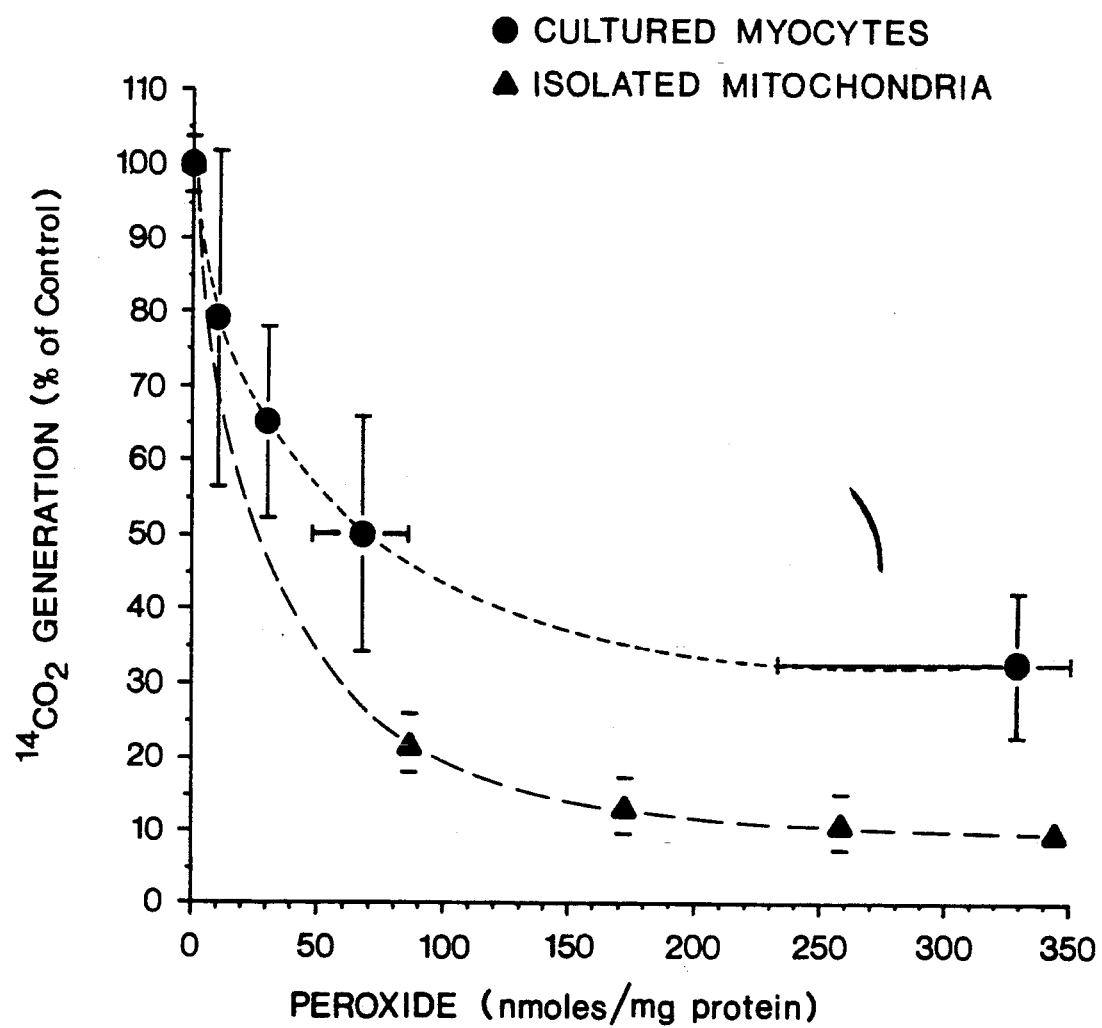
FIG. 6 is a graph showing pyruvate dehydrogenase activity ($^{14}CO_2$ generation) vs. peroxide dose in cultured cardiomyocytes and freshly isolated cardiac mitochondria.

Pyruvate dehydrogenase flux was assayed in isolated cardiac mitochondria as previously described for renal mitochondria in Vlessis, *J. Biol. Chem.* 265:1448-1453, and Vlessis et al., *Biochem. Biophys. Res. Commun.* 170:1281-1287 (1990). The results are shown in FIG. 6, which shows pyruvate dehydrogenase activity ($^{14}CO_2$ generation) vs. peroxide dose in cultured cardiomyocytes and freshly isolated cardiac mitochondria. Enzymatic liberation of $^{14}CO_2$ from [1—$^{14}$C] pyruvate is expressed as percent of control rates obtained in untreated cells or mitochondria. Each symbol represents the mean of values obtained from 4 or 5 separate culture dishes or mitochondrial suspensions. The bracket above, below, right, or left of each symbol includes one standard deviation of the mean.

OTHER EMBODIMENTS

An alternative embodiment of the culture dish is shown in FIG. 4, wherein sidewall 16 includes an annular base 70 having smooth arcuate inner and outer faces, and an annular mating portion 72 having a smooth arcuate inner face and an outer face molded to form a helical thread 74. Collar 22 of cover 18 has a smooth arcuate outer face, but its inner face is molded to present a helical thread 76 that mates in a substantially gas-tight fit with thread 74. The elastic band 36 is not needed with this embodiment because the cover and dish have a self-contained gas-tight mating assembly.

Yet another alternative embodiment of the dish is shown in FIG. 5, wherein sidewall 16 includes an upright annular base 80 that is surmounted by an annular mating portion 82 that has an outer face that inclines toward the interior of the dish, such that portion 82 tapers superiorly. Collar 22 has a cooperatively inclined annular inner face that fits against the inclined face of portion 82 to form a substantially gas-tight seal.

In preferred embodiments, the dishes of FIGS. 15 have a diameter of 30 mm and a sidewall height of 10 mm hence the dish is wider than it is high. Hence, the inside face 20 of cover 18 is spaced in parallel relationship above surface 14 by a distance of 10 mm. The distance between surface 14 and cover 18 can be increased, for example, by 3-5 mm, to provide more space between the tube 42 and media 50. This additional spacing would help decrease any contamination of tube 42 by media 50. As shown in the drawing, the tube 42 is longer than the height of the culture dish between the culture surface 14 and flat inside face of cover 18.

Having illustrated and described the principles of the invention in several preferred embodiments, it should be apparent to those skilled in the art that the invention can be modified in arrangement and detail without departing from such principles. We claim all modifications coming within the spirit and scope of the following claims.

We claim:

1. A device for collecting gas evolved by living cultured cells, comprising:
   a culture dish comprising a culture surface circumscribed by a continuous sidewall;

a removable cover that selectively fits in substantially gas-tight relationship against the sidewall, the cover having a flat inside face;

a container that defines an elongated bore having an open mouth, the container being selectively secured against the inside face of the cover with the bore substantially parallel to the inside face of the cover, the bore being capable of retaining by capillary tension, when the bore is substantially horizontal, a liquid that absorbs carbon dioxide gas; and a liquid held by capillary tension in the bore of the container and that absorbs carbon dioxide gas.

2. The device of claim 1 wherein the inside face of the cover is about 10–15 mm above the culture surface.

3. The device of claim 1 wherein the cover is flat and further comprises an opening that extends through the cover that is sealed by a substantially gas impermeable but needle pervious plastic film adhered to the cover.

4. The device of claim 1 wherein the container is a tubular container that is selectively secured to the inside face of the cover with adhesive tape.

5. The device of claim 1 wherein the cover is held in selectively gas-tight relationship against the sidewall by an elastic band that selectively fits against the sidewall and cover.

6. The device of claim 5 wherein the cover is flat and includes a collar depending from an edge of the cover and circumscribing the inside face of the cover, and matable with an exterior face of the sidewall.

7. The device of claim 1 wherein the cover includes a collar that circumscribes and depends from the inside face of the cover and is matable with the sidewall, and the collar and sidewall are provided with matable helical grooves on the cover and sidewall that are matable in substantially gas-tight relationship.

8. The device of claim 1 wherein the cover includes a collar that depends from and circumscribes the inside face of the cover and is matable with the sidewall, and the cover is holdable in selectively substantially gas-tight relationship against the sidewall by fitting reciprocally tapered surfaces on the collar and sidewall.

9. A device for collecting gas evolved by living cultured cells comprising:

a plastic culture dish comprising a flat culture surface circumscribed by a continuous sidewall comprising a cylindrical inner surface;

a removable flat cover having a flat inside face and a collar depending from the inside face, wherein the collar fits against the sidewall;

sealing means for maintaining the collar in substantially gas-tight relationship against the sidewall;

an opening extending through the flat cover that forms a port through which a needle can be passed, wherein the opening is sealed by a gas impervious film that is penetratable by a needle;

a collector tube having a tapering outer body and a longitudinal bore of sufficiently small diameter to retain by capillary tension, when the bore is substantially horizontal, a liquid that absorbs carbon dioxide gas, wherein the tube is removably secured to the inside face with the bore substantially parallel to the flat inside face; and a liquid in the bore of the tube that absorbs carbon dioxide gas and is retained by capillary tension in the tube.

10. The device of claim 9 wherein the plastic culture dish is wider than it is high.

11. A radiorespirometry method for quantitating an amount of carbon dioxide evolved by living cells, comprising the steps of:

providing a culture dish that comprises a flat culture surface circumscribed by a continuous sidewall, and a removable cover in substantially gas-tight relationship to the sidewall, the cover having a flat inside face against which a collector tube is selectively secured, wherein the tube has a longitudinal bore and a carbon dioxide collecting liquid retained in the bore by capillary action, and the tube is positioned against the inside face with the bore extending substantially parallel to the inside face;

incubating intact cells attached to the culture surface without mechanically disrupting the cells by scraping them from the culture surface;

injecting a sufficient amount of a cell denaturing agent into the dish to terminate the incubation;

removing the cover and detaching the tube from the inside face; and placing the tube into a liquid scintillator and quantitating the amount of $CO_2$ contained in the liquid.

12. The method of claim 11 further comprising the step of replacing the cover after injecting the cell denaturing agent, and continuing to collect $CO_2$.

13. The method of claim 11 wherein the cover is perforated by an opening through the cover that is sealed by a gas impermeable film, and said step of injecting comprises injecting a sufficient amount of a cell denaturing agent through the opening and film into the dish to terminate the incubation before removing the cover and detaching the tube from the inside face.

14. The method of claim 11 wherein the inside face of the cover is 10–15 mm above the culture surface, and the culture surface is wider than the height of the face above the culture surface.

15. The method of claim 14 wherein the culture dish has a diameter of about 30 mm.

16. The method of claim 11 wherein the step of incubating intact cells comprises incubating cardiomyocytes.

17. A radiorespirometry method for quantitating an amount of carbon dioxide evolved by living cells, comprising the steps of:

providing a plastic culture dish that comprises a culture surface circumscribed by a continuous vertical sidewall, and a flat plastic cover in substantially gas tight relationship to the sidewall, the cover having a flat inside face against which a collector tube is selectively secured, and a collar circumscribing and depending from the cover and mating with the sidewall, wherein the tube has a tapering outside body and contains a carbon dioxide collecting liquid that is entirely contained in a tubular bore that extends substantially parallel to the inside face and culture surface and terminates in an open end, the bore retaining therewithin by capillary tension said liquid that absorbs carbon dioxide gas, the cover further including a port opening through the flat cover that is sealed by a substantially gas impermeable but needle pervious film, the distance between the culture surface and inside face being about 10–15 mm;

incubating intact cells attached to the culture surface without mechanically disrupting the cells by scraping them from the culture surface;

inserting a needle through the film sealing the opening in the cover and injecting a sufficient amount of a cell denaturing agent through the needle into the dish to terminate the incubation;

removing the cover and detaching the tube from the inside face; and placing the tube into a liquid scintillator outside of the dish and quantitating the amount of $CO_2$ contained in the liquid.

18. The method of claim 17 wherein the method further comprises the step of mating the collar in substantially gas tight relationship with the sidewall during the incubating step.

19. The method of claim 17 wherein the method further comprises placing a substantially gas impermeable elastic band around the sidewall and collar such that is covers a junction between the sidewall and collar and forms a substantially gas impermeable seal therebetween.

20. The method of claim 17 wherein the collar and sidewall having mating helical threads that mate to form a substantially gas impermeable seal between the collar and sidewall, and the method further comprises the step of mating the threads to form the substantially gas impermeable seal.

21. The method of claim 17 wherein the collar and sidewall have reciprocally tapered surfaces that fit against each other in substantially gas impermeable relationship, and the method further comprises the step of fitting the tapered surfaces against each other to establish a substantially gas impermeable seal during incubation.

* * * * *

UNITED STATES PATENT AND TRADEMARK OFFICE
CERTIFICATE OF CORRECTION

PATENT NO. : 5,324,636
DATED : June 28, 1994
INVENTOR(S) : Bartos et al.

It is certified that error appears in the above-identified patent and that said Letters Patent is hereby corrected as shown below:

Column 1, line 19, "[–$^{14}$C]" should be --[1-$^{14}$C]--;

Column 4, line 44, "([1–$^{14}$]-pyruvate)" should be --([1-$^{14}$C]-pyruvate)--.

Column 5, line 8, "generated $CO_2$" should be --generated $^{14}CO_2$--.

Column 5, line 22, "[1–$^{14}$]" should be --[1-$^{14}$C]--;

Column 5, line 26, "Were" should be --were--;

Column 6, line 17, "[1–$^{14}$]" should be --[1-$^{14}$C]--; and

Column 6, line 45, "FIGS. 15" should be --FIGS. 1-5--.

Signed and Sealed this

Fifteenth Day of November, 1994

Attest:

BRUCE LEHMAN

Attesting Officer

Commissioner of Patents and Trademarks